United States Patent [19]

Le Pecq et al.

[11] 4,045,565

[45] Aug. 30, 1977

[54] 9-HYDROXY ELLIPTICINE

[75] Inventors: Jean Bernard Le Pecq; Claude Paoletti, both of Paris; Nguyen Dat-Xuong, Antony, all of France

[73] Assignee: Etablissement Public dit: Agence Nationale de Valorisation de la Recherche (ANVAR), Neuilly sur Seine, France

[21] Appl. No.: 518,875

[22] Filed: Oct. 29, 1974

[30] Foreign Application Priority Data

Oct. 29, 1973 France .................................. 73.38416

[51] Int. Cl.$^2$ .................. C07D 471/04; A61K 31/395
[52] U.S. Cl. .................................. 424/263; 260/296 P
[58] Field of Search .................................. 260/296 P

[56] References Cited

PUBLICATIONS

Le Pecq et al., C.R. Acad. Sci., Ser. D., vol. 277, pp. 2289-2291 (1973) as abstracted in Chemical Abstracts, vol. 80, Abst. No. 78478h (1974).
Le Pecq et al., Proc. Natl. Acad. Sci. U.S.A., vol. 71, pp. 5078-5082 (1974), as abstracted in Chemical Abstracts, vol. 82, Abst. No. 106193y (1975).
Huu Chanh et al., C.R. Hebd. Seances Acad. Sci., Ser. D, vol. 279, pp. 1039-1042 (1974), as abstracted in Chemical Abstracts, vol. 82, Abst. No. 132961s (1975).
Oustrin et al., C.R. Acad. Sci., Ser. D, vol. 278, pp. 1967 to 1970, (1974), as abstracted in Chemical Abstracts, vol. 81, Abst. No. 58439 (1974).
Wegland et al., Organic Preparations, pp. 194 to 197, Interscience Publishers Inc., NY (1945).
White et al., J. Am. Chem. Soc., vol. 85, pp. 337-343 (1963).
Dalton et al., Chem. Abstracts, vol. 68, Abst. No. 49850v (1968).

*Primary Examiner*—John D. Randolph
*Attorney, Agent, or Firm*—Charles H. Lindrooth

[57] ABSTRACT

9-hydroxy ellipticine, preparation thereof, and use thereof for the treatment of leukemias and solid tumors.

8 Claims, No Drawings

9-HYDROXY ELLIPTICINE

The present invention relates to a new product, 9-hydroxy ellipticine, or 9-hydroxy-5,11-dimethyl-(6H) pyrido [4,3-b] carbazole and a process for obtaining same. The invention further relates to the application of said compound as a medicament or as the active principle of pharmaceutical compositions, notably for the treatment of leukemias and solid tumors. The compound of the invention is most particularly efficacious in the treatment of leukemias. With respect to the treatment of leukemias and solid tumors, the tests on animals, when viewed in the light of work done and results performed on related compounds, support the conclusion that 9-hydroxy ellipticine will prove useful in human therapeutics.

The preparation and therapeutic application of an elipticine derivative, 9-methoxy-ellipticine lactate, has already been described. Recent studies, described in an article by G. Mathe, M. HAYAT, F. de VASSAL, L. Schwarzenberg, M. SCHNEIDER, J. R. SCHLUMBERGER, C. JASMIN and C. ROSENFELD in Rev. Europ. Etudes Clin. Biol. 15, 1970, pp. 541-545 and in an article by J. LE MEN, M. HAYAT, G. MATHE, J. C. GUILLON, E. CHENU, M. HUMBLOT and Y. MASSON in Rev. Europ. Etudes Clin. Biol. 15, 1970, pp. 534-538, have shown that 9-methoxy-ellipticine lactate, apart from an onocostatic action in mouse leukemia and BPS tumors, is effective in acute myeloblastic leukemia but has been found to be ineffective in the treatment of acute lymphoblastic leukemia and Hodgkin's disease; moreover, although it has an immunosuppressive action when administered after the antigen, 9-methoxy-ellipticine lactate does not reveal such an action when administered to man. Methoxy-9 ellipticine is an essential alkaloid of Ochrosia leaves.

Furthermore, both 9-methoxy-ellipticine and other compounds commonly used in human therapeutics for the treatment of certain tumors, such as, for example, bis-betachloroethyl nitroso urea, Amethopterin or methotrexate, 6-mercapto-purine, 5-fluoro-uracile or cyclophosphamide or Endoxan, only reveal substantial antitumor activity at strong doses closed to the lethal dose or LD 50. But it would, on the contrary, be very advantageous, notably in human therapeutics, to be able to administer the active antitumor principles at loses as far removed as possible from the toxic doses.

It has now been found that a new product, 9-hydroxy-ellipticine or 9-hydroxy-5,11-dimethyl-(6H) pyrido [4,3,-b] carbazole has considerably higher antitumor properties with respect to many tumors and particularly mouse 1210 leukemia compared with that of the above-mentioned known compounds.

The new product of the invention has the following planar structural formula:

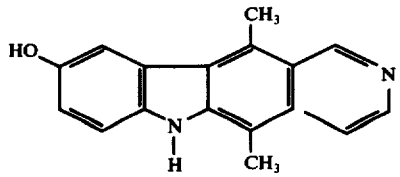

Said compound, 9-hydroxy-ellipticine, corresponding to the empirical formula $C_{17}H_{14}N_2O$, has a molecular weight of 262 and may be called 9-hydroxy-5,11-dimethyl-(6H) pyrido [4,3-b] carbazole according to the official rules governing chemical nomenclature.

In the pure state, 9-hydroxy-ellipticine exists in the form of fine orange coloured crystals melting at a temperature substantially higher than 330° C with decomposition.

It crystalises either with one molecule of methanol or with one mole of water, according to the recrystallization solvent.

Crystallized with a molecule of methanol, 9-hydroxy-ellipticine has the empirical formula $C_{18}H_{18}N_2O_2$ and in its IR spectrum has a line at 3100 cm$^{-1}$ characteristic of the —OH functional group. Its mass spectrum has a very distinct $M+^{262}$ molecular peak.

Thin layer chromatography of hydroxy-ellipticine according to the invention reveals a Rf of 0.44 with alumina as substrate and a benzene ethanol mixture (in a ratio of 28:2) as eluant.

To prepare the said 9-hydroxy-ellipticine, a 9-methoxy-ellipticine demethylation process with, for example, pyridine hydrochloride, glacial acetic acid saturated with hydrochloric acid, gaseous hydrobromic acid or hydroiodic acid is used. It is, however, preferable to effect the demethylation of 9-methoxy-ellipticine in the presence of recrystallized pyridine hydrochloride in redistilled pyridine as, with said demethylation agent, a pure hydroxy-ellipticine is obtained, i.e. free of undesirable by-products.

The demethylation agent should preferably be used in a large molar excess based on the moles of 9-methoxy-ellipticine used.

The starting 9-methoxy-ellipticine can be obtained by extraction from a natural source, or by synthesis (with respect to this see, among others, the articles by J. W. LODER in Aust. J. Chem., 1967, 20, pp. 2715, 2727 and J. POISSON and C. MIET in Ann. Pharm. Franc; 1967, 25 p. 523).

Another object of the invention is an antileukemic and antitumor pharmaceutic composition including a therapeutically effective amount of 9-hydroxy-ellipticine. The said composition can, for example, be in the form of an injectable solution or solid preparations which can be administered per os.

The compound of the invention has been observed to be exceptionally effective in the treatment of leukemias and tumors, notably in the treatment of mouse L 1210 leukemia. This activity can probably be attributed to the strong affinity of the compound of the invention for deoxyribonucleic acid (intercalating effect).

In order to test the antileukemic and antitumor activity of the new compound of the invention, the effect on mouse L 1210 leukemia was used; this experimental tumor, known as mouse L 1210 leukemia, is commonly used for evaluating all the antitumor compounds now used in human therapeutics, as is described, for example, in C. C. ZUBROD in Proc. Nat. Acad. Sci. USA 69, 1972, pp. 1042-1047. This experimentally formed tumoral system permits very accurate quantitative evaluation: of the activity of the compound tested and also, consequently, an objective comparison of the respective activities of various compounds, for example, according to the methods described by H. E. SKIPPER, F. M. SCHABLE Jr. and W. S. WILCOX in Cance Chemother. Rep. 35, 1964, pp. 1-111 and 45, 1965, pp. 5-28.

In practice, mice having received an introperitoneal injection of an inoculum of L 1210 leukemia cells were used, half of them having been subjected to an intraperitoneal injection of a single dose of 9-hydroxy-ellipticine 24 hours after the said tumoral inoculation; the other half of the mice received an injection of an identical volume of an inactive solvent and were used as a control series. The mice were randomized in each experimental series. A first routine experiment enabled the death rate by toxicity to be determined and thus establish the sublethal doses.

According to the convention obtaining in this field, the animals which survived longer than 45 days after inoculation of tumoral cells were considered to be cured.

It was thus possible to determine the death rate due to toxicity resulting from a single injection of different doses of 9-hydroxy-ellipticine (sublethal doses, LD 50 and LD 100) and evaluate the survival rate of a group of animals which has only been injected with a sublethal dose of 9-hydroxy-ellipticine.

The survival rate was calculated from statistical analysis of the experimental results, compared with the results obtained with the control series, according to the well known Mann-Whitely and Wilcoxon methods; the percentage of leukemic cells killed by the treatment applied was calculated by the method described by H. E. Skipper et al in the above-mentioned articles, taking as a basis either increase in the mean survival in the absence of survivors, or the percentage of survivors, as the case may be.

To evaluate the therapeutic activity of the 9-hydroxy-ellipticine of the invention, doses of said compound were expressed basing them on the 30 day sublethal dose which was fixed at 1. Said sublethal dose was in fact easier to determine for the compound of the invention than the LD 10, which it approximates very closely and which is usually taken as a reference for the evaluation of the therapeutic activity of compounds having an antitumor effect (see H. E. Skipper et al. articles mentioned above).

It was thus possible to determine that 9-hydroxy-ellipticine is 100 to 1000 times more active than 9-methoxy-ellipticine.

Comparing the effects of 9-hydroxy ellipticine on L 1210 leukemia with those described in the literature on the same tumoral material, but for the above-mentioned products now commonly used in human therapeutics it was observed that:

in strong doses, approximately the lethal dose, the antitumor activity of 9-hydroxy-ellipticine was at least equal to, and even most often higher than, that of the most active products;

in weak doses, that is to say, at sublethal doses of approximately a few tenths of the lethal dose, the compound of the invention had a very significant and exceptional activity;

Now, it is naturally advantageous to be able to use such active compounds, notably in human therapeutics, at doses as far removed as possible from toxic doses.

The invention is described in greater detail in the following examples which in no way limit it.

EXAMPLE 1

Preparation of 9-hydroxy-ellipticine

A mixture of one part by weight 9-methoxy-ellipticine obtained by extraction from "yellowwood" (Ochrosia maculata) from the island of Reunion, and from 3 to 11 parts by weight of pyridine hydrochloride were heated with gentle reflux for 30 to 90 minutes. The reaction mass became a dark brown colour; it was then poured over crushed ice, the precipitate formed was centrifuged and washed several times with iced water and then recrystallized in methanol. The crystals obtained were orange coloured.

The melting point of the crystalline product was substantially higher than 330° C. The empirical formula of said product, which it was established crystallized with 1 mole methanol, was $C_{18}H_{18}N_2O_2$ which gave the empirical formula $C_{17}H_{14}N_2O$ for pure 9-hydroxy-ellipticine; the molecular weight of the latter being 262, elementary analysis gave:

|  | C% | H% | N% | O% |
|---|---|---|---|---|
| calculated | 73,53 | 5,17 | 9,53 | 10,88 |
| found | 73,50 | 5,35 | 9,48 | 10,48 |

At 3100 cm$^{-1}$ the IR spectrum of the compound obtained gave the line characteristic of the -OH group.

Its mass spectrum revealed a M$^{+262}$ molecular peak and analysis with thin layer chromatography using alumina as a substrate and a 28:2 benzene:ethanol mixture as eluant, gave a Rf of 0.44.

EXAMPLE 2

1-Pharmacological trials relating to the antitumoral activity

An inoculum of $10^2$ to $10^6$ L 1210 leukemia cells was administered by the intraperitoneal way to a large number of 2 to 3 month old DBA/2 strain female mice. 24 hours later, half of said mice received an intraperitioneal injection of a single dose of 9-hydroxy-ellipticine prepared according to example 1 and the same volume of solvent was administered to the other half of the mice by the same way; the latter half of the group of mice was therefore used as the control series.

The mice were randomized in each experimental series, which in all cases comprised 20 to 40 animals.

The number of dead animals was counted evry day at the same time.

Animals surviving for longer than 45 days were considered to be cured.

The 30 day sublethal dose, or 50 mg/kg, was taken as the basis of therapeutic activity of the compound of the invention.

In the following tables I and II are given the results obtained by varying either the number of tumoral inoculum cells (table I) or the dose of 9-hydroxy-ellipticine injected (table II).

TABLE I

The therapeutic effect of a single sublethal dose (50 mg/kg) of 9-hydroxy ellipticine as a function of the number of tumoral cells injected.

| Number of cells injected | Means survival in days of control mice | mean survival in days of treated mice, (cured mice omitted from the calculation) | % mice surviving after 45 days | % Tumoral cells killed by the treatment |
|---|---|---|---|---|
| $10^6$ | 8,8 ± 0,5 | 11,6 ± 0,5 | 0 | 99,60 |
| $10^5$ | 9,7 ± 0,4 | 14,8 ± 2,3 | 0 | 99,99 |

TABLE I-continued

The therapeutic effect of a single sublethal dose (50 mg/kg) of 9-hydroxy ellipticine as a function of the number of tumoral cells injected.

| Number of cells injected | Means survival in days of control mice | mean survival in days of treated mice, (cured mice omitted from the calculation) | % mice surviving after 45 days | % Tumoral cells killed by the treatment |
| --- | --- | --- | --- | --- |
| $10^4$ | 11,0 ± 0,5 | 16,6 ± 2,5 | 7 | 99,97 |
| $10^3$ | 12,4 ± 0,8 | 20,0 ± 4,2 | 44 | 99,92 |
| $10^2$ | 13,5 ± 0,5 | 19,2 ± 5,4 | 70 | 99,60 |

TABLE II

Therapeutic effect of variable doses of 9-hydroxy- ellipticine, for a tumoral inoculum of $10^4$ cells.

| Dose of 9-hydroxy ellipticine injected in a fraction of the sublethal dose 50(mg/kg) | Mean survival in days of control mice | Mean survival in days of treated mice (cured mice omitted from the calculation) | % of mice surviving after 45 days (cured) | % of tumoral cells killed by the treatment |
| --- | --- | --- | --- | --- |
| 0,1 | 11,1 ± 0,4 | 13,0 ± 0,5 | 0 | 97,00 |
| 0,2 | 11,1 ± 0,4 | 13,5 ± 0,4 | 0 | 99,00 |
| 0,4 | 11,1 ± 0,4 | 13,8 ± 0,2 | 0 | 99,30 |
| 0,6 | 11,1 ± 0,4 | 14,0 ± 0,7 | 3 | 99,96 |
| 0,8 | 11,4 ± 0,5 | 15,5 ± 0,8 | 20 | 99,98 |
| 1 | 11,0 ± 0,5 | 16,6 ± 2,5 | 7 | 99,97 |

In all the series of mice treated, the increase in mean survival rate was statistically very clear and significant. Furthermore, it is seen from the above two tables that a large number of mice were cured with 9-hydroxy-ellipticine, whereas in the control series no mice survived for longer than sixteen days.

The results given in the tables further show that a given dose of 9-hydroxy-ellipticine resulted in the destruction of a determined fraction of cells and not in the destruction of a fixed number of cells. This can be deduced from the fact that the percentage of tumoral cells killed by a given dose of 9-hydroxy-ellipticine was almost constant whatever the amount of tumoral cells injected (table I). The percentage of cells killed can therefore be taken as a quantitative measure of the efficacy of the treatment. This enables an objective comparison to be made of the activity of various substances and, among other things, made it possible to establish that 9-hydroxy-ellipticine was much more active than the ellipticine derivatives previously known, and notably more active than 9-methoxy-ellipticine: whereas 0.6 times the infralethal dose of 9-hydroxy ellipticine was capable of killing 99.96% of the tumoral cells, the same dose of 9-methoxy-ellipticine only killed 90% of the tumoral cells.

9-hydroxy ellipticine therefore appears to be 100 to 1000 times more active than its methoxylated derivative.

2-Pharmacological trials relating to the cardiotonic activity

The experiments were conducted on dogs of various breeds and both sexes weighing between 10 and 25 kg.

The animals wwere anesthetized with chloralose (100 mg/kg i.v.).

After preliminary studies which demonstrated the cardiovascular action of 9-hydroxy-ellipticine and enabled the optimal active dose to be determined, 42 dogs were divided into 5 groups for both following studies:

2- 1. Study of the action of 9-hydroxy ellipticine (9-OH-E) on myocardium contractility:

15 dogs were placed under artificial respiration. The contractile power of the heart was recorded by a strain gauge secured to the wall of the right ventricule. The rate of development of the isometric tension of the myocardium was measured with a differentiator. (Hugo Sachs Electronik). The rate of heart beat was recorded with an Offner Beckman cardiotachometer and the ECG with a Cardioline (R) electrocardiograph.

Group I (5 dogs): the animals received 9-OH- E, alone, administered intravenously in a single dose of 1 or 5 or 10 mg/kg.

Group II (5 dogs): the animals were given preliminary intravenous injections of 1 mg/kg dl-propranolol to block the $\beta$-adrenergic receptors. The efficacy of propanolol administered intravenously at 1 mg/kg in blocking $\beta$ adrenergic receptors was tested by the administration of 0.25 mg/kg isoproterenol before and after administration of propanolol. Under the experimental conditions adopted, at least 80 p 100 of the adrenergic receptors were blocked.

Group III (3 dogs): the animals received 1 mg/kg d-propanolol as pretreatment.

Group IV (10 dogs): the animals received a pretreatment of either 1 mg/kg reserpine administered intravenously 24 h before the experiment or 0.1 mg/kg reserpine by the intraperitoneal way 48 h prior to the experiment. In the first case, reserpine induces more than 50 p 100 depletion of NA in the heart, spleen and surrenals, and more than 70 p 100 in the brain and, in the second case, depletion of 99.5 p .100 NA in the atrium. 9-OH- E was administered intravenously to animals of groups II, III, IV, at a rate of 10 mg/kg, the optimal effective dose on myocardium contractility. The contractile power of the heart, df/dt, rate of heart beat, ECG., and arterial blood pressure of animal in groups I, II, III, IV, were recorded simultaneously prior to and after administration of 9-OH-E for one hour. It was thus possible to study their variations as a function of time in response to 9-OH-E.

2-1.1. The effects of 9-hydroxy-ellipticine (group I):

1 mg/kg 9-OH-E administered intravenously did not induce significant modifications of the contractile power of the heart, the rate of development of the isometric tension of the myocardium or the rate of heart beat.

At doses higher than 5 mg/kg administered intravenously, 9-OH-E had a significant cardiostimulant action: this action was weak for intravenous doses of 5 mg/kg; at 10 mg/kg 2 min after administration of 9-OH-E, the increase in the contractile power of the heart was 30 p. 100 greater than the amplitude of initial contractions. From the 10th minute following administration of 9-OH-E, the cardiostimulant action decreased, but it remained about 20 p. 100 higher than the amplitude of the initial cardiac contractions for longer than one hour.

The increase in the amplitude of the contractile power of the heart is accompanied by a more marked increase in the rate of development of the isometric tension of the myocardium.

9-OH-E has no significant effect on the rate of heart beat of the animals treated.

2-1.2 The effects of 9-OH-E after blocking of β-adrenergic receptors (groups II and III).

Dl-propranolol greatly attenuates, or even abolishes, the cardiostimulant action of 9-OH-E (10 mg/kg administered intravenously) where as d propranolol administered under the same experimental conditions did not significantly modify this action.

2-1.3. Effects of 9-OH-E after depletion of catecholamines.

(group IV).

The cardiostimulating action of 9-OH-E was practically abolished when it was administered to animals which have received a pretreatment with reserpine, resulting in a high level of depletion of catecholamines.

2.2 Study of the action of 9-OH-E on respiration and basal metabolism, and on systemic hemodynamics (group V, 11 animals).

Femoral arterial pressure was recorded on the right femoral artery with a Statham P23 AA electromanometer. The ventilatory output and rhythm are measured with a Drager recording volumeter. The air expired is collected in a Douglas bag. Blood $pO_2$, $pCO_2$ and pH, and $pO_2$ and $pCO_2$ of the air expired are measured with the Il meter (R) apparatus. Cardiac output was measured by the Fick method. All the physiological parameters were recorded simultaneously on the Offner Beckman Dynograph (R). These data fed into the computor made it possible to calculate all the systemic hemodynamic, respiratory and metabolic parameters.

The value of each of the parameters was measured for each animal prior to, and 2, 10, 30 and 60 minutes after administration of the product studied. For each of the parameters, the average and standard deviations, as well as the percentage of variation as a function of time, based on control values, were calculated. The averages are compared by the t-test of Studient at a threshold of 5 p. 100.

2. 2.1 The effects of 9-OH-E on respiration and basal metabolism

Intravenous administration of 10 mg/kg 9-OH-E was demonstrated to be a respiratory analeptic in so far as it increased ventilatory output, but it also accelerates ventilatory rhythm: the increase inventilatory output increases with time; 60 min. after administration of 9-OH-E, the ventilatory output of treated animals is about 80 p. 100 higher than that of animals prior to administration of the product.

9-OH-E stimulates both the total oxygen intake and production of $CO_2$; the respiratory quotient of treated animals decreased slightly.

2. 2.2. Effects of 9-OH-E on systemic hemodynamism.

10 mg/kg 9-OH-E administered intravenously does not result in significant modifications in systolic, diastolic, mean and differential arterial pressures, apart from a transient fall in arterial pressure following administration of 9-OH-E. But 9-OH-E markedly lowered the total peripheral resistance and elastic resistance of the arteries.

10 mg/kg 9-OH-E administered intravenously appreciably stimulates cardiac performances: heart output, systolic ejection rate, cardiac and systolic index, work of the left ventricule and work of systolic ejection. The action of 9-OH-E on the cardiac output and index is progressive but durable: at 60 min. after administration of 9-OH-E, both these parameters are 60 p. 100 higher than their initial value and tend to increase further. 9-OH-E has a still greater effect on the systolic ejection output and systolic index. Similarly, it is more active on the work of systolic ejection that on the work of the left ventricule: it first transiently decreases the work of the left ventricule before increasing it. 9-OH-E lowers the tension-time index.

These experiments demonstrate a positive inotropic action of 9-OH-E, 9-OH-E stimulates both the contractile power of the heart and the rate of development of the isometric tension of the myocardium, its effect on the latter being more marked.

9-OH-E results in a great improvement in cardiac performances: it increases cardiac output, systolic ejection output, the cardiac and systolic indices, work of the left ventricule and work of systolic injection. On the other hand, it slightly slows down heart rhythm and decreases the oxygen requirement of the myocardium, 9-OH-E has no significant action on arterial pressures (systolic, diastolic, mean and differential) apart from a transient fall in pressure induced as soon as it is administered.

9-OH-E stimulates the respiration of animals treated; it increases the rate but also speeds up the rhythm.

What I claim is:

1. 9-hydroxy ellipticine or 9-hydroxy-5,11-dimethyl-(6H)-pyrido [4,3-b] carbazole.

2. The composition of claim 1 crystallized in a substantially pure state in the form of orange-coloured crystals melting at a temperature substantially higher than 330° C with decomposition.

3. The composition of claim 1 crystallized with one molecule of methanol or water and having an -OH line at 3100 cm$^{-1}$ in its IR spectrum, a M+$^{262}$ peak in its mass spectrum and giving a Rf of 0.44 in thin layer chromatography on alumina using 28:2 benzene:ethanol mixture as eluant.

4. A process for preparing 9-hydroxy ellipticine comprising demethylating a 9-methoxy-ellipticine using a molar excess of pyridine hydrochloride.

5. The process according to claim 4, wherein 3 to 11 parts by weight of pyridine hydrochloride are used for 1 part by weight of 9-methoxy ellipticine.

6. A pharmacautical composition comprising a therapeutically effective amount of 9-hydroxy ellipticine.

7. A pharmaceutical composition as claimed in claim 6, in the form of an injectable solution or solid preparations for administration per os.

8. A method of cardiac treatment, which comprises using a therapeutically active amount of 9-hydroxy ellipticine.

* * * * *